(12) United States Patent
Stewart

(10) Patent No.: US 6,969,773 B2
(45) Date of Patent: Nov. 29, 2005

(54) FUEL ADDITIVE CONTAINING FERROUS PICRATE PRODUCED BY A PROCESS UTILIZING WIRE

(75) Inventor: David M. Stewart, Taylorsville, UT (US)

(73) Assignee: RDI Construction, South Point, OH (US)

( * ) Notice: Subject to any disclaimer, the term of this patent is extended or adjusted under 35 U.S.C. 154(b) by 397 days.

(21) Appl. No.: 10/150,602

(22) Filed: May 16, 2002

(65) Prior Publication Data

US 2003/0213166 A1    Nov. 20, 2003

(51) Int. Cl.$^7$ .............................. C07F 15/02; C10L 1/22
(52) U.S. Cl. ........................... 556/150; 44/323; 44/367
(58) Field of Search .................. 44/323, 367; 556/150

(56) References Cited

U.S. PATENT DOCUMENTS

| | | |
|---|---|---|
| 2,506,539 A | 5/1950 | Boardman |
| 3,282,858 A | 11/1966 | Simmons |
| 4,073,626 A | 2/1978 | Simmons |
| 4,099,930 A | 7/1978 | Webb |
| 4,129,421 A | 12/1978 | Webb |
| 4,265,639 A | 5/1981 | Scholtz |
| 4,397,654 A | 8/1983 | 'T Hart |
| 4,424,063 A | 1/1984 | Hart |
| 5,087,268 A | 2/1992 | Parish |
| 5,359,103 A | 10/1994 | Elliott et al. |
| 5,562,742 A | 10/1996 | Kolp et al. |
| 5,720,783 A | 2/1998 | Elliott |
| 5,925,153 A | 7/1999 | Riegel |
| 6,670,495 B2 | 12/2003 | Stewart |
| 2003/0213166 A1 | 11/2003 | Stewart |
| 2003/0213167 A1 * | 11/2003 | Stewart ..................... 44/413 |
| 2004/0158089 A1 * | 8/2004 | Elliott et al. ............... 556/146 |

FOREIGN PATENT DOCUMENTS

| | | |
|---|---|---|
| AU | B-63110/90 | 6/1991 |
| AU | B-57904/90 | 9/1991 |
| DE | 27 59 055 A1 | 12/1979 |
| WO | WO 94/26689 | 11/1994 |

* cited by examiner

Primary Examiner—Porfirio Nazario-Gonzalez
(74) Attorney, Agent, or Firm—TraskBritt

(57) ABSTRACT

A fuel additive containing ferrous picrate produced by a process involving placing wire composed of an alloy of iron in any solution of picric acid in a solvent that is known in the art for reacting with iron to produce ferrous picrate. The wire can be suspended in the solution or placed upon the bottom of a reaction vessel that holds the solution. Preferably the wire is loosely coiled, at least when placed upon the bottom of a reaction vessel. Also preferably, after a concentrated fuel additive has been prepared, to the concentrate is added so much of a pre-mix solution produced by the steps of (a) dissolving picric acid in the same kind of solvent that was utilized to produce the solution into which the steel wool was placed and (b) removing water from the precursor to the pre-mix solution thus produced and so much of the same kind of alcohol that was utilized to produce the solution into which the steel wool was placed that the final product produced thereby contains approximately 1.9 percent free picric acid and 15 to 16 percent of the alcohol.

72 Claims, No Drawings

FUEL ADDITIVE CONTAINING FERROUS PICRATE PRODUCED BY A PROCESS UTILIZING WIRE

BACKGROUND OF THE INVENTION

1. Field of the Invention

This invention relates to a fuel additive produced by a process for producing ferrous picrate utilizing wire.

2. Description of the Related Art

There are many patents dealing with process for producing ferrous picrate fuel additives.

These includes U.S. Pat. Nos. 2,506,539; 3,282,858; 4,073,626; 4,099,930; 4,129,421; 4,265,639; 4,424,063; 5,087,268; 5,359,103; 5,720,783; and 5,925,153.

Only U.S. Pat. Nos. 5,087,268 and 5,925,153 employ metallic iron; and these both utilize powdered elemental iron. The large surface area of powdered elemental iron facilitates the desired reaction.

Surprisingly, though, another inventor, whose invention is owned by same entity that owns the present invention, discovered that favorable reaction rates can be obtained using steel wool. Such invention is the subject of a patent application filed concurrently with the present application.

SUMMARY OF THE INVENTION

And even more surprisingly, the present inventor has discovered that wire comprised of an iron alloy can produce favorable reaction rates.

Preferably the wire is loosely coiled and either suspended in the reaction vessel or placed upon the bottom of the reaction vessel.

The product produced by this process does not contain the particles of iron found in fuel additives produced from iron in accordance with the processes of the prior art.

DESCRIPTION OF THE PREFERRED EMBODIMENT

The present process can employ any solution of picric acid in a solvent that is known in the art for reacting with iron to produce ferrous picrate.

Preferably, however, a solution that is approximately three percent picric acid (i.e., three grams of picric acid per one hundred milliliters of solvent) is produced by dissolving picric acid in a solvent. Acceptable solvents are an aromatic solvent such as benzene, toluene, or xylene or a high aromatic petroleum fraction such as Solvent 100, although all other aromatic solvents and high aromatic petroleum fractions disclosed in the art to be used for a similar purpose are also acceptable and will hereinafter simply be termed aromatic solvents and high aromatic petroleum fractions used in the art. A practical percentage which can be achieved within a reasonable time is 2.8 percent. The more picric acid which is dissolved, the better. It is, however, extremely difficult to dissolve significantly more than three percent. The percentage of picric acid which has been dissolved is determined analytically, preferably by titration.

After having combined the picric acid with the solvent, water is removed from the solution using any technique that is well known in the art. Preferably, though, settling is allowed to occur so that the water is vertically separate from the solution of picric acid in solvent. Then the top layer can be removed by decantation or siphoning, or the bottom layer can be removed by draining. One of the various alternate methods for removal is centrifugal separation; another is azeotropic distillation.

The solution resulting from this preferred mixture is termed a pre-mix (as also, for the purposes of this patent application, is any solution of picric acid in a solvent, after such solution has been dewatered, that is prepared in accordance with the art of preparing ferrous picrate; such solution before dewatering is termed a precursor to the pre-mix solution) and has subsequently added to it an aliphatic alcohol. A non-exclusive list of acceptable aliphatic alcohols includes ethanol, isopropanol, and butanol. Butanol is preferred. It is preferable to add the aliphatic alcohol to the pre-mix rather than adding the pre-mix to the aliphatic alcohol in order to prevent the precipitation of some of the dissolved picric acid. Preferably, 25 percent butanol is combined with 75 percent pre-mix on a volume basis.

To the resultant solution some water, preferably 0.1 to 0.5 percent and most preferably approximately 0.1 percent, is added. This is to control the quantity of water since some is necessary for the desired reaction to occur, but an excess amount causes instability and degradation in the product.

Preferably, the solution is agitated after the initial combination of ingredients and each addition of an ingredient.

Wire composed of an alloy of iron is suspended in the solution, either any solution known in the art for producing ferrous picrate from iron or the preferred solution discussed above, or is placed upon the bottom of a reaction vessel that contains the solution. Preferably the wire is loosely coiled, at least when placed upon the bottom of a reaction vessel. Suspension of the wire can be accomplished using any material that will not react with the substances in the solution; stainless steel is, however, preferred for this purpose.

The wire preferably, but not necessarily, contains 0.2 to 5.0 percent, by weight, of carbon, manganese, phosphorous, sulfur, and silica alloyed with the iron.

The solution is preferably agitated after the wire has been introduced. The product resulting from reaction of the picric acid with the wire to produce ferrous picrate is termed a "concentrate." A preferred concentration of iron in the concentrate is 1425 ppm.

It has experimentally been determined, however, that degradation of the product over time is minimized, i.e., stability is maximized, when the solution contains approximately 1.9 percent free (dissolved but unreacted) picric acid and 15 to 16 percent aliphatic alcohol, preferably butanol. A selected concentration of iron less than that of the concentrate is then achieved by combining the requisite amounts of concentrate, pre-mix, and aliphatic alcohol to attain the desired concentration of iron while also containing approximately 1.9 percent free picric acid and 15 to 16 percent of the alcohol. This is termed the final product.

Either the concentrate or the final product is appropriately termed a fuel additive.

A further decrease in degradation is caused by the fact that the use of wire instead of small particles of iron, such as filings or powder, precludes small particles of iron from being in the concentrate and the final product.

The following example illustrates this process.

EXAMPLE 1

A mixture of 22.5 parts of picric acid and 750 parts of Solvent 100 was agitated in a container until the picric acid was dissolved. Then 250 parts of butanol were added to the solution. This was then thoroughly mixed. Next, 1 part of tap water was added to the solution; and the contents were again thoroughly mixed. Then 8 parts of steel wire were suspended in the solution. The contents of the container were then agitated for 1 hour and 35 minutes to produce a ferrous picrate solution containing 1,425 parts per million of ferrous iron.

As used herein the term "preferable" or "preferably" means that a specified element or technique is more acceptable than another but not that such specified element or technique is a necessity.

I claim:

1. A product produced by a process, the process comprising:
   placing a non-powdered alloy of iron in a solution for producing ferrous picrate, wherein the non-powdered alloy of iron comprises from 0.2 to 5.0 percent, by weight, of carbon, manganese, nhosphorous, sulfur, and silica alloyed with the iron, and wherein the product thus produced comprises manganese, phosphorus, sulfur, and silica.

2. The product produced by the process as recited in claim 1, wherein:
   the placing of the non-powdered alloy of iron in the solution is done so that the non-powdered alloy of iron is on the bottom of a container that holds the solution.

3. The product produced by the process as recited in claim 1, wherein:
   the placing of the non-powdered alloy of iron in the solution is done so that the non-powdered alloy of iron is suspended in the solution.

4. The product produced by the process as recited in claim 1, wherein:
   the non-powdered alloy of iron comprises wire that is loosely coiled.

5. The product produced by the process as recited in claim 4, wherein:
   the placing of the wire in the solution is done so that the wire is on the bottom of a container that holds the solution.

6. The product produced by the process as recited in claim 4, wherein:
   the placing of the wire in the solution is done so that the wire is suspended in the solution.

7. The product produced by the process as recited in claim 4, wherein:
   the wire is comprised of 0.2 to 5.0 percent, by weight, of carbon, manganese, phosphorous, sulfur, and silica alloyed with the iron.

8. The product produced by the process as recited in claim 7, wherein:
   the placing of the wire in the solution is done so that the wire is on the bottom of a container that holds the solution.

9. The product produced by the process as recited in claim 7, wherein:
   the placing of the wire in the solution is done so that the wire is suspended in the solution.

10. The product produced by the process as recited in claim 7, with the process further comprising:
    agitating the solution after the wire has been introduced into the solution.

11. The product produced by the process as recited in claim 10, wherein:
    the placing of the wire in the solution is done so that the wire is on the bottom of a container that holds the solution.

12. The product produced by the process as recited in claim 10, wherein:
    the placing of the wire in the solution is done so that the wire is suspended in the solution.

13. The product produced by the process as recited in claim 10, wherein:
    the method for producing the solution into which the wire is placed comprises:
    dissolving picric acid in a solvent selected from the group consisting of aromatic solvents and high aromatic petroleum fractions;
    agitating the solution;
    removing water from the solution;
    adding an aliphatic alcohol to the solution containing the dissolved picric acid;
    agitating the solution;
    adding to the resultant solution 0.1 to 0.5 percent water; and agitating the resultant solution.

14. The product produced by the process as recited in claim 13, wherein:
    the placing of the wire in the solution is done so that the wire is on the bottom of a container that holds the solution.

15. The product produced by the process as recited in claim 13, wherein:
    the placing of the wire in the solution is done so that the wire is suspended in the solution.

16. The product produced by the process as recited in claim 13, with the process further comprising:
    adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

17. The product produced by the process as recited in claim 16, wherein:
    the placing of the wire in the solution is done so that the wire is on the bottom of a container that holds the solution.

18. The product produced by the process as recited in claim 16, wherein:
    the placing of the wire in the solution is done so that the wire is suspended in the solution.

19. The product produced by the process as recited in claim 10, with the process further comprising:
    adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

20. The product produced by the process as recited in claim 19, wherein:
    the placing of the wire in the solution is done so that the wire is on the bottom of a container that holds the solution.

21. The product produced by the process as recited in claim 19, wherein:

the placing of the wire in the solution is done so that the wire is suspended in the solution.

22. The product produced by the process as recited in claim 7, wherein:
the method for producing the solution into which the wire is placed comprises:
dissolving picric acid in a solvent selected from the group consisting of aromatic solvents and high aromatic petroleum fractions;
agitating the solution;
removing water from the solution;
adding an aliphatic alcohol to the solution containing the dissolved picric acid;
agitating the solution;
adding to the resultant solution 0.1 to 0.5 percent water; and
agitating the resultant solution.

23. The product produced by the process as recited in claim 22, wherein:
the placing of the wire in the solution is done so that the wire is on the bottom of a container that holds the solution.

24. The product produced by the process as recited in claim 22, wherein:
the placing of the wire in the solution is done so that the wire is suspended in the solution.

25. The product produced by the process as recited in claim 22, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

26. The product produced by the process as recited in claim 25, wherein:
the placing of the wire in the solution is done so that the wire is on the bottom of a container that holds the solution.

27. The product produced by the process as recited in claim 25, wherein:
the placing of the wire in the solution is done so that the wire is suspended in the solution.

28. The product produced by the process as recited in claim 7, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

29. (previously presented) The product produced by the process as recited in claim 28, wherein:
the placing of the wire in the solution is done so that the wire is on the bottom of a container that holds the solution.

30. The product produced by the process as recited in claim 28, wherein:
the placing of the wire in the solution is done so that the wire is suspended in the solution.

31. The product produced by the process as recited in claim 4, with the process further comprising:
agitating the solution after the wire has been introduced into the solution.

32. The product produced by the process as recited in claim 31, wherein:
the placing of the wire in the solution is done so that the wire is on the bottom of a container that holds the solution.

33. The product produced by the process as recited in claim 31, wherein:
the placing of the wire in the solution is done so that the wire is suspended in the solution.

34. The product produced by the process as recited in claim 31, wherein:
the method for producing the solution into which the wire is placed comprises:
dissolving picric acid in a solvent selected from the group consisting of aromatic solvents and high aromatic petroleum fractions;
agitating the solution;
removing water from the solution;
adding an aliphatic alcohol to the solution containing the dissolved picric acid;
agitating the solution;
adding to the resultant solution 0.1 to 0.5 percent water; and
agitating the resultant solution.

35. The product produced by the process as recited in claim 34, wherein:
the placing of the wire in the solution is done so that the wire is on the bottom of a container that holds the solution.

36. The product produced by the process as recited in claim 34, wherein:
the placing of the wire in the solution is done so that the wire is suspended in the solution.

37. The product produced by the process as recited in claim 34, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

38. The product produced by the process as recited in claim 37, wherein:
the placing of the wire in the solution is done so that the wire is on the bottom of a container that holds the solution.

39. The product produced by the process as recited in claim 37, wherein:
the placing of the wire in the solution is done so that the wire is suspended in the solution.

40. The product produced by the process as recited in claim 31, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

41. The product produced by the process as recited in claim 40, wherein:
the placing of the wire in the solution is done so that the wire is on the bottom of a container that holds the solution.

42. The product produced by the process as recited in claim 40, wherein:
the placing of the wire in the solution is done so that the wire is suspended in the solution.

43. The product produced by the process as recited in claim 40, wherein:
the method for producing the solution into which the wire is placed comprises:
dissolving picric acid in a solvent selected from the group consisting of aromatic solvents and high aromatic petroleum fractions;
agitating the solution;
removing water from the solution;
adding an aliphatic alcohol to the solution containing the dissolved picric acid;
agitating the solution;
adding to the resultant solution 0.1 to 0.5 percent water; and
agitating the resultant solution.

44. The product produced by the process as recited in claim 43, wherein:
the placing of the wire in the solution is done so that the wire is on the bottom of a container that holds the solution.

45. The product produced by the process as recited in claim 43, wherein:
the placing of the wire in the solution is done so that the wire is suspended in the solution.

46. The product produced by the process as recited in claim 43, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

47. The product produced by the process as recited in claim 46, wherein:
the placing of the wire in the solution is done so that the wire is on the bottom of a container that holds the solution.

48. The product produced by the process as recited in claim 46, wherein:
the placing of the wire in the solution is done so that the wire is suspended in the solution.

49. The product produced by the process as recited in claim 46, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

50. The product produced by the process as recited in claim 49, wherein:
the placing of the wire in the solution is done so that the wire is on the bottom of a container that holds the solution.

51. The product produced by the process as recited in claim 49, wherein:
the placing of the wire in the solution is done so that the wire is suspended in the solution.

52. The product produced by the process as recited in claim 1, with the process further comprising:
agitating the solution after the non-powdered alloy of iron has been introduced into the solution.

53. The product produced by the process as recited in claim 52, wherein:
the placing of the non-powdered alloy of iron in the solution is done so that the non-powdered alloy of iron is on the bottom of a container that holds the solution.

54. The product produced by the process as recited in claim 52, wherein:
the placing of the non-powdered alloy of iron in the solution is done so that the non-powdered alloy of iron is suspended in the solution.

55. The product produced by the process as recited in claim 52, wherein:
the method for producing the solution into which the non-powdered alloy of iron is placed comprises:
dissolving picric acid in a solvent selected from the group consisting of aromatic solvents and high aromatic petroleum fractions;
agitating the solution; then removing water from the solution;
adding an aliphatic alcohol to the solution containing the dissolved picric acid;
agitating the solution;
adding to the resultant solution 0.1 to 0.5 percent water; and
agitating the resultant solution.

56. The product produced by the process as recited in claim 55, wherein:
the placing of the non-powdered alloy of iron in the solution is done so that the non-powdered alloy of iron is on the bottom of a container that holds the solution.

57. The product produced by the process as recited in claim 55, wherein:
the placing of the non-powdered alloy of iron in the solution is done so that the non-powdered alloy of iron is suspended in the solution.

58. The product produced by the process as recited in claim 55, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

59. The product produced by the process as recited in claim 58, wherein:

the placing of the non-powdered alloy of iron in the solution is done so that the non-powdered alloy of iron is on the bottom of a container that holds the solution.

60. The product produced by the process as recited in claim 58, wherein:
the placing of the non-powdered alloy of iron in the solution is done so that the non-powdered alloy of iron is suspended in the solution.

61. The product produced by the process as recited in claim 52, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

62. The product produced by the process as recited in claim 61, wherein:
the placing of the non-powdered alloy of iron in the solution is done so that the non-powdered alloy of iron is on the bottom of a container that holds the solution.

63. The product produced by the process as recited in claim 61, wherein:
the placing of the non-powdered alloy of iron in the solution is done so that the non-powdered alloy of iron is suspended in the solution.

64. The product produced by the process as recited in claim 1, wherein:
the method for producing the solution into which the non-powdered alloy of iron is placed comprises:
dissolving picric acid in a solvent selected from the group consisting of aromatic solvents and high aromatic petroleum fractions;
agitating the solution;
removing water from the solution;
adding an aliphatic alcohol to the solution containing the dissolved picric acid;
agitating the solution;
adding to the resultant solution 0.1 to 0.5 percent water; and
agitating the resultant solution.

65. The product produced by the process as recited in claim 64, wherein:
the placing of the non-powdered alloy of iron in the solution is done so that the non-powdered alloy of iron is on the bottom of a container that holds the solution.

66. The product produced by the process as recited in claim 64, wherein:
the placing of the non-powdered alloy of iron in the solution is done so that the non-powdered alloy of iron is suspended in the solution.

67. The product produced by the process as recited in claim 64, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

68. The product produced by the process as recited in claim 67, wherein:
the placing of the non-powdered alloy of iron in the solution is done so that the non-powdered alloy of iron is on the bottom of a container that holds the solution.

69. The product produced by the process as recited in claim 67, wherein:
the placing of the non-powdered alloy of iron in the solution is done so that the non-powdered alloy of iron is suspended in the solution.

70. The product produced by the process as recited in claim 1, with the process further comprising:
adding to the resultant solution, so much of a pre-mix solution produced by (a) dissolving picric acid in the same kind of solvent that was utilized to produce the solution into which the wire was placed and (b) removing water from the precursor to the pre-mix solution thus produced and so much of the same kind of alcohol that was utilized to produce the solution into which the wire was placed that the final product produced contains approximately 1.9 percent free picric acid and 15 to 16 percent of the alcohol.

71. The product produced by the process as recited in claim 70, wherein:
the placing of the non-powdered alloy of iron in the solution is done so that the non-powdered alloy of iron is on the bottom of a container that holds the solution.

72. The product produced by the process as recited in claim 70, wherein:
the placing of the non-powdered alloy of iron in the solution is done so that the non-powdered alloy of iron is suspended in the solution.

* * * * *

UNITED STATES PATENT AND TRADEMARK OFFICE
CERTIFICATE OF CORRECTION

PATENT NO. : 6,969,773 B2  Page 1 of 1
APPLICATION NO. : 10/150602
DATED : November 29, 2005
INVENTOR(S) : David M. Stewart It is certified that error appears in the above-identified patent and that said Letters Patent is hereby corrected as shown below:

In the claims:
CLAIM 1, COLUMN 3, LINE 17, change "nhosphorous," to --phosphorous,--

Signed and Sealed this

Third Day of April, 2007

JON W. DUDAS
*Director of the United States Patent and Trademark Office*